United States Patent [19]

Ezer et al.

[11] Patent Number: 4,563,464
[45] Date of Patent: Jan. 7, 1986

[54] 2-AZABICYCLO(2.2.2)OCTANE DERIVATIVES AND THEIR USE AS IMMUNOSUPPRESSIVE AGENTS

[75] Inventors: Elemer Ezer; Laszlo Szporny; Gyorgy Hajos; Csaba Szantay; Tibor Keve; Gyorgy Fekete; Gabor Megyeri; Tibor Acs; Hedvig Bolcskei, all of Budapest, Hungary

[73] Assignee: Richter Gedeon Vegyeszeti Gyar Rt., Budapest, Hungary

[21] Appl. No.: 625,069

[22] Filed: Jun. 27, 1984

[30] Foreign Application Priority Data

Jun. 29, 1983 [HU] Hungary .................. 2343/83

[51] Int. Cl.[4] .............. A61K 31/445; C07D 221/22
[52] U.S. Cl. .................................... 514/299; 546/112
[58] Field of Search .................. 546/112; 514/299

[56] References Cited
PUBLICATIONS

Robert Morrison and Robert Boyd, "Organic Chemistry," 2nd Ed., Allyn and Bacon, Inc., Boston (1966), Sec. 32.9.

Primary Examiner—Henry R. Jiles
Assistant Examiner—Barbara Cassatt
Attorney, Agent, or Firm—Karl F. Ross; Herbert Dubno

[57] ABSTRACT

The invention relates to new 2-azabicyclo[2.2.2]octane derivatives of the formula (I),

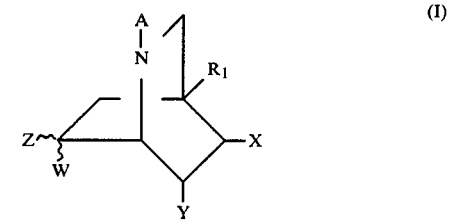

wherein
A is hydrogen, alkoxycarbonyl having from one to 4 carbon atoms in the alkoxy group, phenylalkoxycarbonyl having from one to 4 carbon atoms in the alkoxy moiety, alkyl having from one to 6 carbon atoms, aralkyl containing from one to 4 carbon atoms in the alkyl moiety or substituted acyl,
$R_1$ is hydrogen or alkyl having from one to 4 carbon atoms,
Z is hydrogen or halogen,
X is hydrogen or halogen,
Y is hydrogen, or
X and Y together represent a C—C bond,
W is alkoxycarbonyl having from one to 4 carbon atoms in the alkoxy moiety, cyano, carboxamido or haloformyl, or
if X stands for halogen, X and Y together represent a

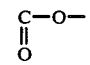

group.

According to another aspect of the invention there is provided a process for the preparation of the above compounds, which are pharmaceutically active, in particular, possess valuable anticonvulsive, vasodilating or gastric acid secretion inhibiting properties. Pharmaceutical compositions containing compounds of the formula (I) are also within the scope of the invention.

4 Claims, No Drawings

2-AZABICYCLO(2.2.2)OCTANE DERIVATIVES AND THEIR USE AS IMMUNOSUPPRESSIVE AGENTS

The invention relates to new 2-azabicyclo-[2,2,2]octane derivatives of the formula (I),

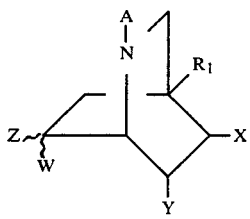

wherein
- A is hydrogen, alkoxycarbonyl having from one to four carbon atoms in the alkoxy group, phenylalkoxycarbonyl having from one to four carbon atoms in the alkoxy moiety, alkyl having from one to six carbon atoms, aralkyl containing from one to four carbon atoms in the alkyl moiety or substituted acyl,
- $R_1$ is hydrogen or alkyl having from one to four carbon atoms,
- Z is hydrogen or halogen,
- X is hydrogen or halogen,
- Y is hydrogen or,
- X and Y together represent a C—C bond,
- W is alkoxycarbonyl having from one to four carbon atoms in the alkoxy moiety, cyano, carboxamido or haloformyl, or
- if X stands for halogen, W and Y together represent a

group

According to another aspect of the invention there are provided processes for the preparation of the above compounds.

The compounds of the formula (I) are themselves biologically active, and possess valuable immunosuppressive, anticonvulsive, vasodilating and gastric acid secretion inhibiting properties. On the other hand, they are also of use in the preparation of other known biologically active compounds having a 2-azabicyclo[2,2,2]octane skeleton such as iboga alkaloids, as well as in the preparation of new compounds having gastric acid secretion inhibiting properties.

According to a yet further feature of the present invention there are provided pharmaceutical compositions comprising, as active ingredient, at least one compound of formula (I) as hereinbefore defined in association with a pharmaceutical carrier or excipient.

In the compounds of the formula (I) the term "alkoxy" alone or as part of another group is used to refer to any straight-chained or branched alkoxy group, having one to four carbon atoms, e.g. a methoxy, ethoxy, n-propoxy, isopropoxy, n-butoxy, isobutoxy, tert.-butoxy group.

A as an alkyl group having from one to 6 carbon atoms may represent a straight-chained or branched $C_{1-6}$ alkyl group, e.g. a methyl, ethyl, n-propyl, isopropyl, n-butyl, isobutyl, tert.-butyl, n-pentyl, isopentyl, n-hexyl or isohexyl group. Such groups, except n- or isopentyl, n- or isohexyl, may also be represented by $R_1$ when this represents a $C_{1-4}$ alkyl group.

The aralkyl groups having one to four carbon atoms in the alkyl moiety represented by A may comprise one or more monocyclic or polycyclic, separate or fused, carbo- or heterocyclic aryl groups, preferably indolyl.

The term "substituted acyl" is used herein to refer to a substituted aryl($C_{1-4}$ alkoxy)carbonyl group, in which the aryl moiety is as defined above, preferably indolyl. The substituents preferably include halogen, lower alkyl and lower alkoxy groups, etc.

Z and X as a halogen may represent fluorine, chlorine, bromine or iodine, preferably chlorine or bromine.

According to the invention compounds of the formula (I), in which A stands for a $C_{1-4}$ alkoxycarbonyl phenyl($C_{1-4}$ alkoxy)carbonyl group, X and Y together represent a C—C bond, $R_1$, Z and W are as defined above, are prepared by reacting a 1,2-dihydropyridine derivative of the formula (II),

in which A and $R_1$ are as defined directly above, with an acrylic acid derivative of the formula (III),

in which W and Z are as defined above. This reaction is a cycloaddition, in which the A group attached to the nitrogen of the compound of the formula (II) is a protecting group, which stabilizes the dihydropyridine structure. As a result, the compounds are more resistant to atmospheric oxygen and are easier to handle.

Compounds of the formula (I) obtained, in which W represent a haloformyl group and the other substituent are as defined in the previous paragraph, may be hydrolyzed to the corresponding acids (if desired, without separation), and may then be converted into the corresponding halolactones of the formula (I), in which W and Y together represent a

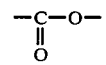

group and X halogen [$a_1$].

Compounds of the formula (I) obtained by the reaction of the compounds of formula (II) and (III), in which A is a $C_{1-4}$ alkoxycarbonyl or phenyl($C_{1-4}$ alkoxy)carbonyl group, X and Y represent a C—C bond, Z is halogen, W is a ($C_{1-4}$ alkoxy)carbonyl, cyano or carboxamido group and $R_1$ has the same meaning as defined above, may be reduced on their halogen (Z) to yield the corresponding compounds of formula (I), in which Z is hydrogen [$a_2$].

Compounds of the formula (I), in which A is a $C_{1-4}$ alkoxycarbonyl or phenyl($C_{1-4}$ alkoxy)carbonyl group, X and Y together represent a C—C bond, Z is hydrogen or halogen, W stands for a haloformyl group and $R_1$ is as defined above, may be converted, if desired without separation, into a corresponding ester derivative by adding an aliphatic alcohol having from one to four carbon atoms [$a_3$].

If desired, compounds of the formula (I), in which A is a $C_{1-4}$ alkoxycarbonyl or phenyl($C_{1-4}$ alkoxy)carbonyl group, X and Y together represent a C—C bond, Z is hydrogen or halogen, W stands for a cyano group and $R_1$ has the same meaning as defined above, can be hydrolyzed into a corresponding acid amide (W=carboxamido) [$a_4$].

Compounds of the formula (I), in which A represents a $C_{1-4}$ alkoxycarbonyl or phenyl($C_{1-4}$ alkoxy)carbonyl group, X and Y together represent a C—C bond and $R_1$, Z and W are as defined in connection with the formula (I), can be converted into the corresponding 2-azabicyclo-[2.2.2]oct-5-ene derivatives of the formula (I), in which A is hydrogen, by elimination of the protecting group A under acidic conditions [$b_1$]. If desired, the compounds obtained may be converted into acid addition salts.

Alternatively, the protecting group A may be eliminated by catalytic hydrogenation with an excess amount of hydrogen. In this reaction, simultaneously with the elimination of the protecting group the X-Y double bond is saturated, and if Z=halogen, it is replaced by hydrogen [$b_2$].

The double bond is the compounds of the formula (I), in which A is hydrogen, X and Y together represent a C—C bond, and $R_1$, Z and W are as defined above, or in their acid addition salts can be saturated also by catalytic hydrogenation with a calculated amount of hydrogen [$c_1$]. In this alternative, the halogen in place of Z remains unchanged.

If desired, compounds of the formula (I), in which A is hydrogen and X, Y, $R_1$, Z and W are as defined above, or acid addition salts thereof, can be converted into the corresponding compounds of the formula (I), in which A stands for a $C_{1-6}$ alkyl, aralkyl containing 1 to 4 carbon atoms in the alkyl moiety or substituted acyl, by alkylation or acylation.

For the preparation of the 2-azabicyclo[2.2.2]octane (isoquinuclidine) skeleton there are more alternative processes known in the art. The first method was published by Ferber and Brückner [Chem. Ber. 76 B, 1019–1027 (1943)].

The disadvantage of the isoquinuclidine syntheses developed by Ferber and Brückner, starting from cyclohexane aminocarboxylic acid derivatives, is that the ring closure is performed at very high temperatures. A further disadvantage is that an isoquinuclidone is obtained, in which the selective elimination of the oxygen of the acid amide is a difficult problem.

Furstoss et al. [Tetrahedron Letters 1970, 1263; ibid 1972, 993–996; Bull. Soc. Chim. France 1974, 2485–94; Can. J. Chem. 1976, 3569–79; C.R. Acad. Sci. Ser. C. 1971, 273 (6) 478–80] used N-chloro-N-methylaminomethyl-cyclohexene derivatives as a starting material for the ring closure reaction. The drawback of this method is that in addition to the desired isoquinuclidine also other azabicyclo derivatives are formed.

Isoquinuclidine derivatives can be obtained also from cyclic compounds having a different skeleton such as aziridines (J. Am. Chem. Soc. 1967, 5046–48; ibid 1968, 1650–51; French Patent Specification No. 1,572,766), 1-azido-norbornane (J. Org. Chem. 1971, 2864–69); 1-N,N-dichloroaminoapocamphame (J. Am. Chem. Soc. 1972, 7599–7600; ibid 1973, 3646–51) by ring transformation. These reactions again result in the formation of more by-products.

The isoquinuclidine skeleton is most frequently prepared by the Diels-Alder reaction. If the dienophil contains the nitrogen, it is generally reacted with cyclohexadiene. In the study of this reaction type Cava et al. made a pioneer work. By reacting methylene diurethane with cyclohexadiene, in the presence of borotrifluoride they prepared 2-carbethoxy-2-azabicyclo[2.2.2]oct-5-ene (Chem. Ind. 1964, 1422–23; J. Org. Chem. 1965, 1422–23; J. Org. Chem. 1965, 3772–75).

According to a further variant of the above process various compounds of the type R'R''C=NR''' are used as a dienophile (Acta Chem. Scand. 1968, 2585–90; Tetrahedron Letters 1976, 3309–11).

Krow studied the cycloaddition reactions of dienophiles of the type R'CH=NR (J. Chem. Soc. 1973, 5273–80; Tetrahedron Letters, 1974, 2977–81; J. Org. Chem. 1977, 2486–91; Tetrahedron Letters 1978, 1971–74).

If the diene contains the nitrogen necessary for the formation of the isoquinuclidine skeleton, generally a substituted 1,2-dihydropyridine is reacted with various dienophiles, which include maleic acid derivatives, e.g.
maleic acid (Izv. Akad. Nauk, SSSR Ser. Khim. 1964, 1322–24),
maleic acid anhydride (Izv. Akad. Nauk. SSSR Ser. Khim. 1964, 1322–24; J. Am. Chem. Soc. 1961, 449–53; J. Org. Chem. 1962, 320–21),
maleic imide (J. Org. Chem. 1962, 1439–41);
fumaric acid derivatives, e.g. methyl fumarate (Tetrahedron Letters 1977, 4129–32);
acrylic acid derivatives, e.g. methyl acrylate (J. Med. Chem. 1972, 374–78), ethyl acrylate (J. Med. Chem. 1977, 682–86; U.S. Pat. No. 4,100,164; Canadian Patent Specification No. 1,052,785),
acryl nitrile (Helv. Chim. Acta 1962, 1344–51; Tetrahedron Letters 1966, 6385–91; ibid. 3383–86; Chem. Comm. 1969, 88–89, U.S. Pat. No. 3,816,439, Japanese Patent Specification No. 7,519,770);
methyl vinyl ketone (J. Am. Chem. Soc. 1965, 2073–75, ibid. 1966, 3090–109; Tetrahedron Letters 1977, 4299–300); and
acroleine (Tetrahedron Letters 1979, 2485–88).

Japanese scientists, Hongo et al. published a new synthesis route for the preparation of isoquinuclidone compounds: they reacted 2-piperidone with various dienophile (Tetrahedron Letters, 1969, 2465–68; Chem. Pharm. Bull. 1970, 925–31; ibid. 1972, 226–31; Japanese Patent Specification No. 7,413,799; Heterocycles 1977, 267–68, Chem. Pharm. Bull. 1979, 670–75).

As a summary of the above cycloaddition reactions for the preparation of an isoquinuclidine skeleton it can be concluded that the nitrogen-containing dienophils are generally difficult to prepare.

The reactions starting from 2-pyridine or its derivatives as nitrogen-containing dienes also do not provide considerably better results, since these reactions yield the corresponding isoquinuclidone compounds, where the selective elimination of superfluous oxygen function is a further problem.

The Diels-Alder reactions starting from dihydropyridine derivatives are somewhat more convenient, since the starting pyridine derivatives can easily be prepared.

We have surprisingly found that compounds having a 2-azabicyclo[2.2.2]octane skeleton can be prepared from readily accessible starting materials with a good yield by reacting an N-alkoxycarbonyl- or N-aralkoxycarbonyl-1,2-dihydropyridine with an acrylic acid or 2-haloacrylic acid derivative. Further derivatives can be prepared by modification of the 7-substituent of the 2-azabicyclo[2.2.2]oct-5-ene derivative obtained. In this manner e.g. ester, halolactone, cyano or acid amide derivatives can be obtained. In addition, the double bond of the 2-azabicyclo[2.2.2]octene derivative can be saturated by hydrogenation.

If desired, the protecting group can be eliminated from the nitrogen of the 2-azabicyclo[2.2.2]oct-5-ene derivatives obtained, and the obtained, unprotected compounds can be isolated in the form of a salt. If desired, the elimination of the protecting group and the saturation of the double bond of the 2-azabicyclo[2.2.2]oct-5-ene derivatives can be performed simultaneously, and from the unprotected octene or octane derivatives or their acid addition salts new N-alkyl, N-aralkyl and N-acyl derivatives can be prepared by conventional alkylation, aralkylation or acylation reactions.

According to the invention N-alkoxycarbonyl- or N-aralkoxycarbonyl-1,2-dihydropyridines of the formula (II) are used as starting materials. Said compounds may be prepared by the method of Fowler (J. Org. Chem. 1972, 1321–23). Preferably N-ethoxycarbonyl- or N-benzyloxycarbonyl-1,2-dihydropyridine is employed, as a solution in an inert solvent, preferably acetonitrile. According to a preferred embodiment, acrylic acid derivatives or 2-haloacrylic acid derivatives of the formula (III), preferably 2-chloroacrylic acid chloride, 2-chloroacryl nitrile or methyl acrylate, are added to the solution. Alternatively, the dihydropyridine derivatives of the formula (II) may be dissolved in the excess of the dienophiles of the formula (III).

The reaction is performed at room temperature or—in the case of less reactive dienophiles—at slightly elevated temperature, e.g. 60°–90° C., under stirring. The cycloaddition reaction is monitored by spectroscopy or thin layer chromatography.

If the cycloaddition reaction is carried out with an acrylic acid chloride of the formula (III), the acid chloride derivative is converted into the corresponding ester by adding a corresponding alcohol, preferably one having from one to four carbon atoms, into the reaction mixture, which is then stirred for several hours and evaporated.

From the evaporation residue obtained by the above reaction variants the new 2-azabicyclo[2.2.2]oct-5-ene derivatives of the formula (I) may be isolated by several extraction or chromatographic purification steps.

When halolactones of the formula (I) are to be prepared (W and Y together stand for a

group and X is halogen), cycloaddition is carried out with an acid chloride of the formula (III), and the product obtained is converted into the corresponding acid by adding water to the reaction mixture. From the organic solution, by an aqueous-alkaline extraction, preferably carried out with a saturated potassium hydrocarbonate solution, a corresponding salt of the carboxylic acid derivative of the formula (I) is obtained, which is then converted into the desired halolactone by adding the corresponding halogen, preferably bromine or a potassium iodide/iodine solution, to the aqueous solution. The precipitated halolactane of the formula (I) is recrystallized from a conventional organic solvent, preferably ethanol.

To prepare the acid amides of the formula (I), a nitrile of the formula (I) is dissolved in a water-miscible organic solvent, preferably dimethyl sulfoxide, and an aqueous solution of a strong base, preferably potassium hydroxide, is added to the solution. The mixture is stirred for several hours, the precipitated acid amide of the formula (I) is filtered off, and if desired, is recrystallized from a conventional organic solvent, preferably ethanol.

If in a compound of the formula (I), in place of Z halogen is to be replaced by hydrogen, the compound of the formula (I) is reduced, preferably by boiling with zinc in a glacial acetic acid-containing solution.

If desired, the "A" alkoxy- or aralkoxycarbonyl group protecting the nitrogen of the 2-azabicyclo[2.2.2]oct-5-ene derivative can be eliminated as follows:

By treating the N-alkoxy- or N-aralkoxycarbonyl compounds of the formula (I) in an acidic medium, preferably in a glacial acetic acid solution containing hydrogen bromide, the corresponding N-unprotected compounds are obtained, without affecting the substituents Z, W, X, Y and $R_1$. The obtained compounds of the formula (I) may then be converted into their acid addition salts in a known manner.

If in the compounds of the formula (I), in which X and Y together represents a C—C bond, the elimination of the "A" alkoxy- or aralkoxycarbonyl protecting group is to be performed simultaneously with the saturation of the double bond of the N-alkoxy- or N-aralkoxycarbonyl-2-azabicyclo[2.2.2]oct-5-ene compound, the reaction is carried out by catalytic hydrogenation, preferably in the presence of a palladium-on-charcoal or Raney nickel catalyst, with an excess amount of hydrogen. If in the starting compound used in this reaction Z stands for halogen, it is replaced by hydrogen simultaneously with the elimination of the "A" protecting group and the saturation of the double bond. If desired, these compounds can also be converted into a corresponding acid addition salt.

If compounds of the formula (I), in which the nitrogen atom is unprotected, X and Y stand for hydrogen and Z is halogen, are to be prepared, one can start from oct-5-ene derivatives of the formula (I), in which the nitrogen is unprotected, X and Y together represent a C—C bond and Z is halogen. In this case catalytic hydrogenation is carried out with a calculated amount of hydrogen, preferably using palladium-on-charcoal as a catalyst. In this reaction the double bond of the 2-azabicyclo[2.2.2]oct-5-ene derivative derivative is saturated, but in place of Z the halogen atom remains unchanged. If desired, the compounds obtained can be converted into the corresponding acid addition salts.

The unprotected 2-azabicyclo[2.2.2]octane derivatives of the formula (I) obtained by an acidic, preferably glacial acetic acid/hydrogen bromide, treatment or by catalytic hydrogenation, or acid addition salts thereof can be N-alkylated by dissolving them in a polar organic solvent, preferably in an alcohol or acetonitrile, and treating with an organic base, preferably triethyl amine. To the solution obtained a corresponding alkyl or aralkyl halide is added, and the mixture is allowed to stand at room temperature. The progress of the reaction is monitored by thin layer chromatography, whereupon the reaction mixture is evaporated, the salt of the precipitated amine is filtered off, and the N-alkyl- or N-aralkyl-2-azabicyclo[2.2.2]octane derivative is isolated by evaporation of the mother liquor and, if desired, recrystallization from a conventional organic solvent or solvent mixture, if desired, after further purification by chromatography.

The 2-azabicyclo[2.2.2]octane derivatives, which contain no protecting group on the nitrogen, or their acid addition salts can be acylated by techniques conventionally used in the synthesis of peptides: the corresponding base can be set free from an acid addition salt and the acylation can be performed by the aid of a mixed anhydride formed from an organic acid, preferably 3-indolylacetic acid, with pivalyl chloride. The reaction is preferably carried out by dissolving the acid employed, preferably indolylacetic acid, in a dipolar aprotic solvent, preferably dimethyl formamide, adding an organic base, preferably triethyl amine, to the solution, cooling the solution, preferably to $-5°$ to $-10°$ C., adding the pivalyl chloride dropwise, and then a solution of an acid addition salt of the 2-azabicyclo[2.2.2]octane derivative to be acylated preferably in dimethyl formamide or triethyl amine, at low temperature, preferably between 0° C. and $-5°$ C. The reaction mixture is stirred at room temperature, the precipitated triethyl amine salt is filtered off and the mother liquor is evaporated under reduced pressure. The evaporation residue is dissolved in a water-immiscible solvent, preferably ethyl acetate or a chlorinated hydrocarbon, washed with water, dried over magnesium sulfate, evaporated, the precipitated crystals are filtered off, washed, dried and, if desired, recrystallized from a solvent or solvent mixture, preferably methanol or a mixture of n-hexane and ethyl acetate.

Acylation may be carried out also with indolylacetyl chloride in a dichloromethane medium, in the presence of triethyl amine, at room temperature, but also with indolylacetic acid anhydride, in an acetonic medium.

The invention is elucidated in detail by the aid of the following non-limiting Examples.

EXAMPLE 1

2-Benzyloxycarbonyl-4-ethyl-7-chloro-7-methoxycarbonyl-2-azabicyclo[2.2.2]oct-5-ene 21.4 g. (0.2 moles) of 3-ethyl-pyridine are dissolved in 250 ml. of absolute methanol. To the solution 7.5 g. (0.2 moles) of powdered sodium tetrahydroborate are slowly added below $-65°$ C., under vigorous stirring in argon atmosphere, followed by the addition of 28.8 ml. (34.1 g., 0.2 moles) of benzyl chloroformate. The reaction is strongly exothermic. When the addition is complete, the reaction mixture is stirred for an additional hour, whereupon it is carefully heated up to room temperature. The reaction mixture is evaporated in vacuo. The evaporation residue is dissolved in 200 ml. of ether and washed with 100 ml. of water. The aqueous phase is extracted with two additional 100-ml. portions of ether. The combined ethereal phases are washed with 20 ml. of a 1% aqueous acetic acid solution. The pH of the aqueous solution is about 5-6 after the extraction. The ethereal phase is dried over magnesium sulfate, and evaporated in vacuo. The evaporation residue is a mixture of N-benzyloxycarbonyl-1,2-, 1,4- and 1,6-3-ethyl-dihydropyridine isomers.

UV spectrum (methanolic solution): $\lambda_{max}=305$ nm 1,2- and 1,6-3-ethyl-dihydropyridine; $\lambda_{max}=260-270$ nm unreacted 3-ethyl-pyridine; $\lambda_{max}=230-240$ nm 1,4-dihydropyridine. The evaporation residue weighs 36.7 g. (0.153 moles).

IR spectrum: 1700 $cm^{-1}=N-C=O$; 1470 $cm^{-1}$ phenyl; 1100 $cm^{-1}$ C—O—C; 700 $cm^{-1}$; phenyl.

t.l.c. (Kieselgel 60 $F_{154}$, eluent: 10:1 mixture of benzene and acetone, development: in UV light of 254 nm or iodine vapor): $R_f=0.84$ (1,2 and 1,6 isomers). The evaporation residue is dissolved in 150 ml. of absolute acetonitrile, and 24.4 g. (0.194) of 2-chloroacrylic acid chloride and 0.1 g. of hydroquinone are added to the solution. The completion of the cycloaddition is shown by the disappearance of the $\lambda_{max}=305$ nm peak in the UV spectrum. Thereafter, 150 ml. of absolute methanol are added to the reaction mixture, which is then stirred at room temperature for three hours. The pH of the acidic solution is adjusted to 8-9 by addition of triethyl amine under cooling, and it is then evaporated in vacuo. The evaporation residue is dissolved in 100 ml. of benzene, and washed with 50 ml. of water. The benzene phase is dried over magnesium sulfate, filtered and evaporated in vacuo. 59.9 g. of an oily product are obtained, which is then chromatographed on a Kieselgel 60 (0.063–0.2 mm.) column by using a 10:1 mixture of benzene and acetone as an eluent.

Yield: 19.3 g. (35% based on 3-ethyl-pyridine).

IR spectrum (film): 1700 $cm^{-1}=N-O$; 1470 $cm^{-1}$ phenyl; 1100 $cm^{-1}$ C—O—C; 700 $cm^{-1}$ phenyl.

t.l.c. (Kieselgel 60 $F_{254}$, eluent: a 10:1 mixture of benzene and acetone, development: in UV light of 254 nm or in iodine vapor): $R_f=0.85$.

EXAMPLE 2

2-Benzyloxycarbonyl-4-ethyl-7-chloro-7-cyano-2-azabicyclo[2.2.2]oct-5-ene 50 g. (0.2 moles) of 3-ethyl-(N-benzyloxycarbonyl)-1,2-dihydropyridine, contaminated with the 1,4- and 1,6-isomers, are prepared as described in Example 1. It is then dissolved in 60 g. (0.69 moles) of 2-chloroacryl nitrile together eith 1 g. of hydroquinone. The reaction mixture is protected from light and stirred on an oil bath of 70° C. for 70 hours. The completion of the cycloaddition is shown by the disappearance of the $\lambda_{max}=305$ nm peak in the UV spectrum. The reaction mixture is evaporated in vacuo, on a water bath of 50°-60° C., the residual oil is dissolved in 50 ml. of benzene, washed with 50 ml. of water and subsequently with two 50-ml. portions of benzene. The benzene phase is dried over magnesium sulfate and evaporated in vacuo to yield an oily residue. It is the column chromatographed on a 30-fold amount of Kieselgel 60 (0.063–0.2 nm), using a 10:1 mixture of benzene and acetone as an eluent. The $R_f>0.75$ fractions are combined, evaporated and column chromatogrpahed again on a 40-fold amount of a Kieselgel 60 (0.063–0.2 nm), with a 1:1 mixture of benzene and chloroform as an eluent. The product obtained at $R_f=0.56$ is isolated.

Yield: 8.5 g. (0.0257 moles), 13% based on the starting 3-ethyl-pyridine.

t.l.c. (Kieselgel 60 $F_{254}$, eluent: 10:1 benzene/acetone, $R_f=0.812$; 1:1 benzene/chloroform $R_f=0.56$; development in iodine vapor or in UV light of 254 nm.

IR spectrum (film) $cm^{-1}$: 2300—CN; 1700 N—C=O; 1470 Ph; 700 Ph.

NMR spectrum (CDCl$_3$) ppm: 7.3 (5 aromatic H-s); 6.3–6.4 (d, $H_1^5+H_1^6$); 5.15 (S benzyl —CH$_2$—); 5,05 (d, $H_1^1$).

EXAMPLE 3

N-Benzyloxycarbonyl-7-chloro-7-methoxycarbonyl-2-azabicyclo[2.2.2]oct-5-ene 118.5 g. (1.5 moles) of absolute pyridine are dissolved in 1000 ml. of absolute methanol, whereupon 57 g. (1.5 moles) of powdered sodium borohydride are carefully added at a temperature below −65° C., followed by the addition of 248 ml. (298 g., 1.75 moles) of benzyl chloroformate. The reaction is strongly exothermic. When the addition is complete, the mixture is stirred for an additional hour at −70° C., and is then carefully heated up to room temperature. The evaporation residue is dissolved in 400 ml. of ether, and washed with 400 ml. of water, 100 ml. of a 0.1n aqueous hydrochloric acid solution and subsequently with two additional 100-ml. portions of water. The pH of the aqueous phase is about 5–6 after the extraction. The ethereal phase is dried over magnesium sulfate and evaporated.

UV spectrum of the evaporation residue, containing a mixture of 1,2- and 1,4-dihydropyridine isomers in methanolic solution: $\lambda_{max}=305$ nm 1,2-dihydropyridine, $\lambda_{max}=260-270$ nm unreacted pyridine, $\lambda_{max}=2$-30–240 nm 1,4-dihydropyridine.

The 248 g. of the evaporation residue obtained are dissolved in 700 ml. of acetonitrile, and 192 g. (1.54 moles) of 2-chloroacrylic acid chloride and 5 g. of hydroquinone are added. The completion of the cycloaddition is shown in the spectrum by the disappearance of the $\lambda_{max}=305$ nm peak. Thereafter 400 ml. of methanol are added to the mixture, which is allowed to stand at room temperature for three hours. The pH of the acidic solution is adjusted to 8–9 with triethyl amine, under cooling, and it is then evaporated. The evaporation residue is dissolved in 500 ml. of benzene and washed with 100 ml. of water. The benzene phase is dried over magnesium sulfate and evaporated. 442 g. of an oily product are obtained as an evaporation residue, which is chromatographed on a Kieselgel 60 (0.063–0.2 mm) column, using a 10:1 mixture of toluene and ethyl acetate as an eluent.

Yield: 95 g. (18.9%, 0.284 moles)

Melting point: 85° C.

t.l.c. (Kieselgel 60 plate, eluent: 10:1 benzene/ethyl acetate, development in iodine vapor): $R_f=0.6$ IR spectrum: 1720 cm$^{-1}$ ester C=O; 1690 cm$^{-1}$ lactame C=O.

NMR spectrum: 2.75 ppm (s—OCH$_3$), 5.2 ppm (s, benzyl —CH$_2$—), 6.3 ppm (m olefin H-s), 7.4 ppm (aromatic H-s).

EXAMPLE 4

N-Benzyloxycarbonyl-7-chloro-7-cyano-2-azabicyclo[2.2.2]oct-5-ene

N-benzyloxycarbonyl-1,2-dihydropyridine prepared from 15.8 g. (0.2 moles) of pyridine as described in Example 3 are dissolved in 100 ml. of acetonitrile. 34 g. (0.4 moles) of α-chloro-acrylnitrile and 2 g. of hydroquinone are added to the solution, which is then stirred at 80° C. for 30 hours. The completion of cycloaddition is verified by the disappearance of the peak at $\lambda_{max}=305$ nm in the UV spectrum. The reaction mixture is evaporated in vacuo. The evaporation residue is dissolved in 150 ml. of benzene and washed with 30 ml. of water. The benzene solution is dried over magnesium sulfate and evaporated in vacuo. The crude product is chromatographed on a Kieselgel 60 (0.063–0.2 mm) column, using a 10:1 mixture of toluene and ethyl acetate as an eluent.

Yield: 14 g. (23.2%)

Melting point: 68° C.

t.l.c. (Kieselgel 60 plate, eluent: 10:1 benzene/ethyl acetate, development in iodine vapor): $R_f=0.6$ NMR spectrum: 5.2 ppm (s benzyl —CH$_2$—); 6.5 ppm (m olefin H-s), 7.4 ppm. (aromatic H-s).

EXAMPLE 5

2-Benzyloxycarbonyl-7-bromo-7-methoxycarbonyl-2-azabicyclo[2.2.2]oct-5-ene

To 40 g. (0.2 moles) of N-benzyloxycarbonyl-1,2-dihydropyridine prepared as described in Example 3, 38 g. (0.23 moles) of freshly prepared methyl α-bromoacrylate and 2 g. of hydroquinone are added. The reaction mixture is allowed to stand at room temperature for 48 hours, under protection from light. The completion of the cycloaddition is shown by the disappearance of the $\lambda_{max}=305$ nm from the UV spectrum. The reaction mixture is evaporated to an oily residue in vacuo, on a water bath of 40°–50° C., and extracted from three 40-ml. portions of a benzene/brine mixture. The benzene phase is dried over magnesium sulfate and evaporated in vacuo, whereupon it is column chromatographed on a 30-fold amount of Kieselgel (0.063–0.2 mm), using a 10:1 mixture of benzene and ethyl acetate for the elution.

Yield: 8 g. (0.01 moles), 11% based on the starting pyridine t.l.c. (Kieselgel 60 F$_{254}$, Merck Art. 5735; eluent: 10:1 benzene/ethyl acetate): $R_f=0.75$ IR spectrum (film) cm$^{-1}$: 1740 C=O; 1700 N—C=O, 1405 and 705 monosubstituted phenyl, 1250 —O—CH$_3$.

NMR spectrum (CDCl$_3$) ppm: 7.3 [s, Ar(t$^5$)]; 6.4 (m H$^5$, H$_1^6$); 5.2 (benzyl CH$_2$); 4.05 (m, H$_1^1$) 3.65 (OCH$_3$ s).

EXAMPLE 6

N-Ethoxycarbonyl-7-chloro-7-cyano-2-azabicyclo[2.2.2]oct-5-ene

Following the procedure described in Example 3 but using 19.1 ml. (21.7 g., 0.2 moles) of ethoxycarbonyl chloride instead of benzyloxycarbonyl chloride, N-ethoxycarbonyl-1,2-dihydropyridine is prepared, which is then further treated as described in Example 4. The title compound is obtained.

NMR spectrum: 6.56 and 6.63 (m, 5H and 6H); 3.08 ppm (m, 4H).

Yield: 11.8 g. (24.6%).

EXAMPLE 7

N-Benzyloxycarbonyl-4-ethyl-7-methoxycarbonyl-2-azabicyclo[2.2.2]oct-5-ene

Following the procedure described in Example 1, starting from 0.2 moles of 3-ethyl-pyridine about 35–40 g. of 1,2-dihydro-3-ethyl-pyridine are obtained, which are then dissolved in 150 ml. of methyl acrylate together with 0.1 g. of hydroquinone. The reaction mixture is boiled for 10 days, i.e. until the $\lambda_{max}=305$ nm peak disappears from the UV spectrum (peak characteristic of dihydropyridine). The reaction mixture is evaporated in vacuo, at 40°–50° C., and the oily residue is isolated by chromatography on a Kieselgel 60 (0.063–0.2 mm) column, using a 10:1 mixture of benzene and acetone as an eluent.

Yield: 24 to 25 g. (0.072–0.075 moles), 33–40%.

t.l.c.: Kieselgel 60 PF$_{254}$, eluent: 10:1 benzene/acetone, development in iodine vapor or with UV light of 254 nm: R$_f$=0.75.

IR spectrum (film) cm$^{-1}$: 1680 acid amide carbonyl, 1820 ester carbonyl, 1470 phenyl.

EXAMPLE 8

2-Benzyloxycarbonyl-5-exo-bromo-6-endo-hydroxy-7-exo-chloro-2-azabicyclo[2.2.2]octane-7-endo-carboxylic acid γ-lactone Following the procedure described in Example 3 17.0 g. (0.08465 moles) of N-benzyloxycarbonyl-1,2-dihydropyridine are prepared. The product is dissolved in 150 ml. of absolute acetonitrile, and 18 ml. (0.187 moles) of freshly prepared α-chloroacrylic acid chloride and 0.2 g. of hydroquinone are added. The reaction mixture is stirred at room temperature overnight. The completion of the addition is controlled by the UV spectrum, by monitoring the disappearance of the $\lambda_{max}$=305 nm peak, which is characteristic of the 1,2-dihydro compound. To the homogenous acetonitrile solution 30 ml. of distilled water are added, and the mixture is stirred for 30 minutes. The organic phase is extracted with three 150-ml. portions of a saturated potassium bicarbonate solution, which contains 10 g. of ammonium chloride in 100 ml. of the solution. The combined aqueous phases are extracted with five 30-ml. portions of dichloromethane, and the organic solvent is eliminated from the aqueous phase in vacuo.

Into the solvent-free aqueous phase about 2 ml. of bromine are added dropwise, with stirring, until the yellow color of the solution disappears and the precipitation ceases. The excess bromine in the solution is bound by adding an aqueous solution of 2–3 g. of sodium thiosulfate. The precipitate is filtered off, dissolved in 50 ml. of ethanol, and the bromine present in the precipitate is bound by adding a small amount of an aqueous sodium thiosulfate solution. The product is crystallized from the solution by cooling.

Yield: 6.0 g. (0.015 moles) of a crystalline powder (15%)

Melting point: 130°–131° C.

t.l.c. (Kieselgel G, eluent: 10:1 benzene/acetone, development: by iodine vapor): R$_f$=0.65

IR spectrum: KBr cm$^{-1}$ C=O, 1800 C=O 1720, monosubstituted phenyl 1405 and 705

NMR spectrum (CDCl$_3$) ppm: 7.38 (Ar—H$_5$); 5.25 (benzyl —CH$_2$—, s); 5.1–4.8 (H$_1{}^1$ and H$_1{}^6$); 4.2 (H$_1{}^5$ d); 4.1 (H$_1{}^5$ d); 4.1 and 3.5 (H$_1{}^3$, d); 2.5 (H$_1{}^4$+H$_2{}^8$).

EXAMPLE 9

2-Benzyloxycarbonyl-4-ethyl-5-exo-bromo-6-endo-hydroxy-7-exo-chloro-2-azabicyclo[2.2.2]octane-7-endo-carboxylic acid γ-lactone 40.6 g. (0.2 moles) of N-benzyloxycarbonyl-1,2-dihydro-3-ethyl-pyridine prepared as described in Example 1 are dissolved in 100 ml. of absolute acetonitrile, 24.6 g. (0.24 moles) of freshly prepared 2-chloroacrylic acid chloride and 0.2 g. of hydroquinone are added to the solution. The reaction mixture is stirred for one day, under protection from light. The progress of the reaction is controlled by UV spectrum analysis. When at $\lambda_{max}$=305 nm the peak corresponding to 1,2-dihydro-3-ethyl-pyridine disappears, the reaction is complete. The homogenous acetonitrile solution is cooled to 10° C., thereafter 100 ml. of distilled water are added under stirring, and the mixture is stirred for two hours. The aqueous and organic phases are separated. The organic phase is cooled to 10° C. and 40 ml. of a 25% potassium bicarbonate solution is added dropwise, until pH 8. The aqueous phase is separated from the acetonitrile phase and is extracted with two 100-ml. portions of dichloromethane. The solvent traces are then eliminated in vacuo, on a water bath of 30° to 35° C. Into the aqueous phase kept at 40° C. by the aid of the water bath bromine is added dropwise, under continuous stirring until the color of the solution gets yellow. The precipitated yellowish solid is dissolved by adding 100 ml. of dichloromethane, and the system is extracted with a 10% aqueous sodium thiosulfate solution until it becomes colorless. The dichloromethane phase is separated, dried over magnesium sulfate, filtered and evaporated in vacuo.

Yield: 16 to 17 g. of an oil, which gives 4 t.l.c. spots.

t.l.c. (Kieselgel 60, eluent: 10:1 mixture of benzene and acetone, development: in iodine vapor): the desired product is obtained at R$_f$=0.53.

By column chromatographing the crude product on a 30-fold amount of a Kieselgel 60 (0.063–0.2 mm), using a 10:1 mixture of benzene and acetone for the elution, only about 10% of the starting oil can be isolated as the desired product. At R$_f$=0.22 a carboxylic acid containing the carbonyl group in equatorial position is obtained, and also the other spots correspond to various carboxylic acid derivatives, on the basis of the IR spectrum Yield: 1.6 to 1.7 g. (0.00374–0.0042 moles).

Appearance: yellowish oil

IR spectrum (film) cm$^{-1}$: C=O lactone 1820, C=O benzyloxycarbonyl, 1720, monosubstituted phenyl 1405 and 705.

NMR spectrum (CDCl$_3$) ppm: 7.38 (Ar—H$_5$); 5.25 (benzyl—CH$_{2S}$); 5.1–4.8 (H$_1{}^1$ and H$_1{}^6$); 4.2 (H$_1{}^5$, d); 1.3 (ethyl triplet).

EXAMPLE 10

2-Benzyloxycarbonyl-7-chloro-7-carboxamido-2-azabicyclo[2.2.2]oct-5-ene 3.2 g. (0.01 moles) of N-benzyloxycarbonyl-7-chloro-7-cyano-2-azabicyclo[2.2.2]oct-5-ene are dissolved in 10 ml. of dimethyl sulfoxide, and to this solution a solution of 0.45 g. (0.025 moles) of water and 1.4 g. (0.025 moles) of potassium hydroxide, prepared at 100° C., is added, under vigorous stirring. The reaction is monitored by this layer chromatography. The starting material is used up in about 3 hours. The reaction mixture is diluted to 25-fold of its volume with distilled water, under vigorous stirring. The precipitated oil becomes a well filterable precipitate in several hours. The precipitate is filtered off and washed with two 5-ml. portions of distilled water. After drying, the precipitate is recrystallized from 3 ml. of ethanol to yield 1.4 g. (0.0043 moles, 43%) of the title compound. Appearance: white crystals Melting point: 134°–137° C.

t.l.c. (Kieselgel 60 F$_{254}$ plate, eluent: 8:4:2 mixture of benzene, chloroform and ethanol; development: in iodine vapor or in UV light of 254 nm): R$_f$=0.64.

According to the elementary analysis the product contains chlorine, bound with a covalent bond.

IR spectrum (KBr) cm$^{-1}$: 3400–3300 NH, 2870–2900 CH$_2$, 1680–1660 acid amide.

NMR spectrum (CDCl$_3$) ppm: 7.3 (s ArH$_5$); 6.4 (m$_1$ H$_1^5$++H$_1^6$); 6.0 (m, NH$_2$) can be replaced by heavy water, 5.2 (benzyl CH$_2$); 5.0 (m H$_1^1$).

EXAMPLE 11

N-benzyloxycarbonyl-4-ethyl-7-methoxycarbonyl-2-azabicyclo[2.2.2]oct-5-ene 1.5 g. (0.004 moles) of 2-benzyloxycarbonyl-4-ethyl-7-chloro-7-methoxycarbonyl-2-azabicyclo[2.2.2]oct-5-ene prepared according to Example 1 are dissolved in 20 ml. of glacial acetic acid, and 2.5 g. of zinc are added to the solution. The reaction mixture is refluxed in argon atmosphere for three hours. When the complete amount of starting material is used up, the reaction mixture is cooled to room temperature, zinc is filtered off, the mother liquor is evaporated to an oil, and the zinc is washed with 20 ml. of water and 20 ml. of chloroform. The aqueous phase is added to the oil, and the mixture obtained is extracted with three 30-ml. portions of chloroform. The combined chloroformic solutions are dried over magnesium sulfate, filtered and evaporated.

Yield: 1.2 g. (0.0036 moles) 90% t.l.c. (Kieselgel 60 PF$_{254}$; eluent: 10:1 benzene/acetone; development: in iodine vapour or in UV light at 254 nm):

IR spectrum cm$^{-1}$: 1470 pH; 1680 acid amide carbonyl; 1720 ester carbonyl.

Halogen content: none

EXAMPLE 12

7-Chloro-7-methoxycarbonyl-2-azabicyclo[2.2.2]oct-5-ene hydrobromide 10 g. (0.03 moles) of 7-chloro-7-methoxycarbonyl-2-azabicyclo[2.2.2]oct-5-ene prepared according to Example 3 are dissolved in a mixture of 60 ml. of glacial acetic acid and 30 ml. of a 4–5N solution of hydrogen bromide in glacial acetic acid. The mixture is allowed to stand at room temperature for 10 minutes, and is then evaporated. The evaporation residue is dissolved in 5 ml. of acetone and 300 ml. of ether are added to the solution. The precipitated crystalline material is filtered off.

Yield: 8 g. (94%)
Melting point: 188° C.
IR spectrum: 1720 cm$^{-1}$ ester C=O
NMR spectrum: 3.75 ppm (s —OCH$_3$); 6.2–6.5 ppm (olefin H-s).

EXAMPLE 13

7-Chloro-7-cyano-2-azabicyclo[2.2.2]oct-5-ene hydrogen bromide 5.0 g. (0.0165 moles) of N-benzyloxycarbonyl-7-chloro-7-cyano-2-azabicyclo[2.2.2]oct-5-ene are dissolved in a mixture of 30 ml. of glacial acetic acid and 15 ml. of a 4–5N glacial acetic acid/hydrogen bromide mixture. The reaction mixture is allowed to stand at room temperature for 10 minutes, and is then evaporated. The evaporation residue is crystallized from acetone.

Yield: 2.0 g. (0.0081 moles) 49%
Melting point: 224° to 226° C.
IR spectrum: 2220 cm$^{-1}$ C≡N
NMR spectrum (DMSO, d$_6$): 4.5 ppm (d H$_1^1$); 5.8–6.6 (m H$_5^1$+H$_6^1$).

EXAMPLE 14

4-Ethyl-7-chloro-7-methoxycarbonyl-2-azabicyclo[2.2.2]oct-5-ene hydrobromide 16 g. (0.044 moles) of N-benzyloxycarbonyl-7-chloro-7-methoxycarbonyl-2-azabicyclo[2.2.2]oct-5-ene are dissolved in a mixture of 57 ml. of glacial acetic acid and 114 ml. of a 5N solution of hydrogen bromide in glacial acetic acid. The reaction mixture is allowed to stand at room temperature for a half to one hour. The progress of the reaction is monitored by thin layer chromatography. The mixture is then evaporated in vacuo, on a water bath of 40°–50° C. The obtained oily product is triturated with ether and decanted. The residual oil is chromatographed on a Kieselgel 60 (0.0063–0.2 mm.) column, using a 8:4:2 mixture of benzene, chloroform and ethanol as an eluent. The products obtained at R$_f$=0.1 and R$_f$=0.2, respectively, are collected. The two products differ in the configuration of the carbomethoxy group.

Yield: 7.2 g. (53%)

t.l.c. (Kieselgel 60 F$_{254}$; eluent: 10:1 benzene/acetone; development in iodine vapor): R$_f$=0.6.

Under the same conditions, except that the eluent is a 8:4:2 mixture of benzene, chloroform and ethanol: R$_f$=0.1 and 0.2.

EXAMPLE 15

4-Ethyl-7-chloro-7-cyano-2-azabicyclo[2.2.2]oct-5-ene hydrobromide 1 g. of N-benzyloxycarbonyl-4-ethyl-7-chloro-7-cyano-2-azabicyclo[2.2.2]oct-5-ene are dissolved in a mixture of 2 ml. of glacial acetic acid and 0.1 ml. of a 5.3N solution of hydrogen bromide in glacial acetic acid. The mixture is allowed to stand at room temperature for half an hour, under exclusion of moisture. The mixture is evaporated in vacuo on a water bath of 40° C., and three-times 20 ml. of acetone and then two-times 10 ml. of methanol are evaporated off. The evaporation residue contains in addition to the desired product also the corresponding acid, obtained by hydrolysis of the cyano group. The two products are separated on a Kieselgel 60 (0.063–0.2 mm.) column, using a 8:4:2 mixture of benzene, chloroform and ethanol as an eluent.

Yield: 0.1 g. (0.00035 moles, 12%) of the title compound.

t.l.c. (Kieselgel 60 F$_{254}$; eluent; a 8:4:2 mixture of benzene, chloroform and ethanol): R$_f$ acid=0.14; R$_f$ nitrile=0.44.

IR spectrum (KBr) cm$^{-1}$: 3330 NH, 2300 C≡N.

NMR spectrum (CDCl$_3$ ppm: 6.1 (m H$_1^5$+H$_1^6$); 4.2 (d, H$_1^1$); 1.2 (t ethyl CH$_3$).

EXAMPLE 16

7-Bromo-7-methoxycarbonyl-2-azazbicyclo[2.2.2]oct-5-ene hydrobromide 8.0 g. of N-benzyloxycarbonyl-7-bromo-7-methoxycarbonyl-2-azabicyclo[2.2.2]oct-5-ene are dissolved in 40 ml of dichloromethane, and the solution is saturated with hydrogen bromide gas under cooling for five minutes. After saturation the mixture is allowed to stand for another five minutes, whereupon it is evaporated to yield an oily residue, which is then crystallized from acetone.

Yield: 4.0 g. (0.0125 moles, 60%).

t.l.c. (Kieselgel 60 F$_{254}$; eluent: a 8:4:2 mixture of benzene, chloroform and ethanol; development in iodine vapor): R$_f$=0.55.

IR spectrum (KBr) cm$^{-1}$: 1740 C=O; 1250 OCH$_3$.

EXAMPLE 17

7-Chloro-7-carboxamido-2-azabicyclo[2.2.2]oct-5-ene hydrobromide 2.0 g. (0.0075 moles) of N-benzyloxycarbonyl-7-chloro-7-carboxamido-2-azabicyclo[2.2.2]oct-5-ene are dissolved in 4 ml. of glacial acetic acid, and 3 ml. of a 5.6N solution of hydrogen bromide in glacial acetic acid is added. After standing for half an hour, the solution is evaporated in vacuo, on a water bath of 40°–50° C. From the oily residue three 40-ml. portions of methanol are eluminated by evaporation. The oily residue is crystallized from a 2:1 mixture of acetone and ethanol.

Yield: 1.5 g. (0.0055 moles, 74%)
Appearance: crystalline white powder
Melting point: 210° to 253° C.

t.l.c. (Kieselgel 60 F$_{254}$; eluent: a 8:4:2 mixture of benzene, chloroform and ethanol; development in iodine vapor): R$_f$=0.1.

IR spectrum (KBr) cm$^{-1}$: 3400–3300 NH; 2900–2800 CH$_2$, 1680 amide I, 1580 amide II.

NMR spectrum (CDCl$_3$) ppm (from base): 6.5 (m H$_1^6$+H$_1^5$), 3.8–3.9 (m, H$_1^1$).

EXAMPLE 18

6-Methoxycarbonyl-2-azabicyclo[2.2.2]octane hydrochloride 10.1 g. of N-benzyloxycarbonyl-7-chloro-7-methoxycarbonyl-2-azabicyclo[2.2.2]oct-5-ene are dissolved in a mixture of 40 ml. of dichloromethane and 60 ml. of methanol. 1.0 g. of a palladium-on-charcoal catalyst is prehydrogenated in 20 ml. of methanol, and the clear solution of the material to be hydrogenated is added in a closed system. Hydrogen is bubbled through the solution under intensive stirring, for about 8 hours. The progress of the reaction is monitored by measuring the carbon dioxide content of the gas bubbled through the solution or by t.l.c.

R$_f$ starting material: 0.9–1.0; R$_f$ chloroester: 0.1; R$_f$ ester: 0.2

When the hydrogenation is complete, the catalyst is filtered off, washed with a small amount of methanol, the pH of the mother liquor is adjusted to 2 by methanolic hydrogen chloride solution, and the mixture is evaporated. To the residue 50 ml. of acetone are added, and it is evaporated to about half of its volume. The crystallization of the product is very slow, it takes about one week in a refrigerator. The product is then filtered off, and washed with two 5-ml. portions of cold acetone.

Yield: 4.8 g. (0.0235 moles, 78%)
Melting point: 139°–141° C.

t.l.c. (Kieselgel 60 F$_{254}$; eluent: 7:3 benzene/acetone; development in iodine vapor): R$_f$ starting material>R$_f$ product.

IR spectrum (KBr): 1720 =C=O, 1250 cm$^{-1}$ —OCH$_3$ $^1$H-NMR (CDCl$_3$, base) 4.05 (m, 1H, H-1); 3.65 (s, 3H, OCH$_3$ OCH$_3$).

EXAMPLE 19

5-Exo-bromo-6-endo-hydroxy-7-exo-chloro-2-azabicyclo[2,2.2]octane-7-endo-carboxylic acid γ-lactone hydrobromide 6.0 g. (0.015 moles) of 2-benzyloxycarbonyl-5-exo-bromo-6-endo-hydroxy-7-exo-chloro-2-azabicyclo[2.2.2]ctane-7-endo-carboxylic acid γ-lactone are dissolved in 150 ml. of chloroform. The solution is cooled to 0° C. and saturated with hydrogen bromide gas, in about 15 minutes. The hydrogen bromide solution is allowed to stand overnight, when the desired product precipitates as a white crystalline material. It is filtered off, washed with two 10-ml. portions of chloroform and dried.

Yield: 3.1 g. (0.009 moles, 60%)
Melting point: 207° to 209° C.

IR spectrum (KBr) cm$^{-1}$: 1800 C=O; 3450 N—H

NMR spectrum (CDCl$_3$) ppm: 4.9 (2xd H$_1^6$); 4.24 (broad d M$_1^5$); 3.6 (2xd H$_1^1$); 3.55 and 3.12 (H$_2^3$ AB multiplet).

EXAMPLE 20

4-Ethyl-5-exo-bromo-6-endo-hydroxy-7-exo-chloro-2-azabicyclo[2.2.2]octane-7-endo-carboxylic acid γ-lactone hydrobromide 16.0 g. of crude 4-ethyl-5-exo-bromo-6-endo-hydroxy-7-exo-chloro-2-benzyloxycarbonyl[2.2.2]octane-7-endo-carboxylic acid γ-lactane prepared according to Example 9 are dissolved in 100 ml. of dichloromethane, and the solution is saturated with hydrogen bromide gas in 30 minutes, under cooling. The reaction mixture is allowed to stand overnight. Thereafter, it is evaporated in vacuo, on a water bath of 40° C., and four 100-ml. portions of acetone are evaporated off the solution. The evaporation residue is chromatographed on a 30-fold amount of Kieselgel, using a 10:1 mixture of benzene and acetone for the elution. The product is then crystallized from absolute ethanol.

Yield: 2.2 to 3.0 g.
Appearance: white, crystalline powder

IR spectrum (KBr) cm$^{-1}$: C=O 1820; N—H 3450

NMR spectrum (CDCl$_3$, base) ppm: 4.4 (d H$_1^5$); 3.45 (triplet, H$_1^1$), 3.3 (m H$_2^3$); 2.4 (m H$_2^8$).

EXAMPLE 21

6-Chloro-6-methoxycarbonyl-2-azabicyclo[2.2.2]octane hydrobromide 8.5 g. (0.03 moles) of 7-chloro-7-methoxycarbonyl-2-azabicyclo[2.2.2]oct-5-ene hydrobromide are dissolved in 85 ml. of methanol. 0.85 g. of a 10% palladium-on-charcoal catalyst are prehydrogenated in 15 ml. of methanol, and a clear solution of the starting material to be hydrogenated is added in a closed system. Hydrogenation is carried out in a closed system, the progress of the reaction is monitored by measuring the hydrogen consumption. When the calculated amount of hydrogen is used up, the reaction is terminated. When the reaction is not terminated timely, the reaction proceeds further and the chlorine is replaced by hydrogen. The catalyst is filtered off, the solution is evaporated. A crystalline material is obtained, which is triturated in about 20 ml. of acetone, and allowed to stand overnight in a refrigerator. The precipitate is filtered off on the next day, pulpified with two 5-ml. portions of cold acetone, and dried.

Yield: 7 g. (0.0244 moles, 82%)
Melting point: 181° to 183° C.

EXAMPLE 22

2-(n-Butyl)-7-chloro-7-methoxycarbonyl-2-azabicyclo[2.2.2]oct-5-ene 9.6 g. (34.0 mmoles) of 7-methoxycarbonyl-7-chloro-2-azabicyclo[2.2.2]oct-5-ene hydrobromide, 4.78 g. (34.8 mmoles) of n-butyl bromide and 13.6 g. (134.5 mmoles) of triethyl amine are dissolved in 100 ml. of methanol. The solution is allowed to stand for two days. The progress of the reaction is monitored by thin layer chromatography, using a Kieselgel 60 $F_{254}$ plate, and a 8:4:2 mixture of benzene, chloroform and ethanol for the elution. The development is performed in iodine vapor. $R_f$ product: 0.9; $R_f$ starting material (base): 0.5. The reaction mixture is evaporated, the evaporation residue is triturated with about 200 ml. of n-hexane. The precipitated triethyl amine hydrochloride and hydrobromide, resp. is filtered off the hexane solution, and washed with n-hexane. The hexane mother liquor is evaporated. The evaporation residue is separated into its components by column chromatography, carried out on a Kieselgel 60 (0.063–0.2 mm) column, and using a 8:4:2 mixture of benzene, chloroform and ethanol as an eluent.

Yield: 2.1 g. (24.0%), oil
IR spectrum (film): 1720 cm$^{-1}$ ester C=O
NMR spectrum (CDCl$_3$) ppm: 6.2 and 6.5 (m $H_1^5+H_1^6$); 3.85 (d, $H_1^1$); 3.7 (s —OCH$_3$).

EXAMPLE 23

N-(n-Butyl)-7-chloro-7-cyano-2-azabicyclo[2.2.2]oct-5-ene 1.0 g. of 7-chloro-7-cyano-2-azabicyclo[2.2.2]oct-5-ene hydrobromide are dissolved in 5 ml. of absolute methanol, and 0.5 g. of triethyl amine and subsequently 0.5 g. (3.65 mmoles) of n-butyl bromide are added to the solution. The progress of the reaction is monitored by thin layer chromatography, using a Kieselgel 60 $F_{254}$ plate and a 8:4:2 mixture of benzene, chloroform and ethanol for the elution. $R_f$ starting material (base): 0.53; $R_f$ product: 0.95. (The development carried out in iodine vapor or in UV light of 254 nm). The reaction mixture is evaporated in vacuo, and chromatographed on a 30-fold amount of a Kieselgel 60 (0.063–0.2 mm.) column, using a 8:4:2 mixture of benzene, chloroform and ethanol for the elution.

Yield: 0.342 (0.00152 moles), 38%
t.l.c. (Kieselgel 60 $F_{254}$; eluent: 8:4:2 mixture of benzene, chloroform and ethanol; development in iodine vapor of UV light of 254 nm): $R_f=0.95$.
NMR spectrum (CDCl$_3$) ppm: 6.7 (m, $H_1^5+H_1^6$); 4.0 (d, d $H_1^1$); 3.5 (d, d$H_1^4$).

EXAMPLE 24

N-[2-(3'-Indolyl)-ethyl]-7-chloro-7-methoxycarbonyl-2-azabicyclo[2.2.2]oct-5-ene 6.0 g. (21.2 mmoles) of 7-chloro-7-methoxycarbonyl-2-azabicyclo[2.2.2]oct-5-ene hydrobromide, 6.0 g. (27 mmoles) of tryptophyl bromide and 25 ml. (18.0 g., 0.18 moles) of triethyl amine are dissolved in 80 ml. of absolute methanol. The solution is allowed to stand at room temperature for one day. The progress of the reaction is monitored by thin layer chromatography, using a Kieselgel 60 plate, 10:2 mixture of toluene and ethyl acetate as an eluent, and carrying out the development in iodine vapor. $R_f$ product: 0.5.

The reaction mixture is evaporated in vacuo. To the evaporation residue 300 ml. of ethyl acetate are added, and the precipitated solid triethyl amine hydrobromide is filtered off. The mother liquor is evaporated. The obtained evaporation residue, which is about 7 g. of an oily product, is crystallized from a mixture of 50 ml. of ethyl acetate and 2–3 ml. of n-hexane. The mother liquor of the product is subjected to column chromatography on a Kieselgel 60 (0.063–0.2 mm.) column, using a 10:1 mixture of toluene and ethyl acetate as an eluent, and the product is crystallized from a mixture of n-hexane and ethyl acetate as described hereinabove.

Yield: 3.5 g. (48.6%)
Melting point: 128°–130° C.
IR spectrum (KBr): 1720 cm$^{-1}$ ester C=O, 3400 cm$^{-1}$ indole N—H
NMR spectrum, ppm: 7.9 (indole N—H); 7.6 (m aromatic H); 6.2–6.5 (m, $H_1^5+H_1^6$); 3.8 (s —OCH$_3$).

EXAMPLE 25

N-[2-(3'-Indolyl)-ethyl]-7-chloro-7-cyano-2-azabicyclo[2.2.2]oct-5-ene 0.9 g. of tryptophyl bromide are dissolved in 20 ml. of absolute acetonitrile, and 1.0 g. (0.00403 moles) of 7-chloro-cyano-2-azabicyclo[2.2.2]oct-5-ene hydrobromide and 2.4 ml. of absolute triethyl amine are added to the solution. The homogenous solution obtained is stirred for 3 days, under exclusion of light and moisture. The progress of the reaction is monitored by thin layer chromatography. On a Kieselgel 60 $F_{254}$ plate, using a 10:1 mixture of benzene and acetone as an eluent, $R_f$ tryptophyl bromide is 0.86, $R_f$ product is 0.76. The reaction mixture is evaporated in vacuo, on a water bath of 30° to 40° C. The evaporation residue is dissolved in 15 ml. of ether, and extracted with two 5-ml. portions of aqueous ammonia (pH=10). The ethereal phase is dried over magnesium sulfate, and evaporated in vacuo. The obtained oily product is crystallized from 3 ml. of methanol.

Yield: 0.71 g. (0.002324 moles), 55%
Melting point: 126° to 128° C.
t.l.c. (Kieselgel 60 $F_{254}$; eluent: 10:1 benzene/acetone; development: in UV light of 254 nm or in iodine vapor) $R_f=0.76$
IR spectrum (KBr) cm$^{-1}$: 2300 C≡N, 3300 indole NH
NMR spectrum (CDCl$_3$) ppm: 3.8 (d, $H_1^1$), 6.2–6.8 (m $H_1^5+H_1^6$), 7.05–7.7 (m Ar H+indole $H_1^2$).

EXAMPLE 26

N-[2-(3'-Indolyl)-ethyl]-6-chloro-6-methoxycarbonyl-2-azabicyclo[2.2.2]octane 3.84 g. (0.013 moles) of 6-chloro-6-methoxycarbonyl-2-azabicyclo[2.2.2]octane hydrobromide, 3.05 g. of tryptophyl bromide and 5.55 g. (0.052 moles, 7.6 ml.) of triethyl amine are dissolved in 35 ml. of absolute methanol, and the solution is allowed to stand at room temperature for two days. The reaction mixture is evaporated, and to the evaporation residue a mixture of 70 ml. of benzene and 35 ml. of water is added. The organic phase is separated, and washed with two 15-ml. portions of water. The combined aqueous phases are extracted with 15 ml. of benzene. The combined benzene phases are dried over magnesium sulfate, decolored with charcoal, and evaporated in vacuo. From the evaporation residue 25 ml. of ethanol are eliminated by evaporation, and the residueal solid is crystallized from 3 ml. of ethanol. The mother liquor is evaporated, and the residue is crystallized from isopropanol.

Yield: 1.5 g. (0.0043 moles), 33%.

EXAMPLE 27

N-[2-(3'-Indolyl)-ethyl]-7-chloro-6-hydroxy-5-bromo-2-azabicyclo[2.2.2]octane-7-carboxylic acid γ-lactone 0.689 g. (0.0027 moles) of 7-chloro-6-hydroxy-5-bromo-2-azabicyclo[2.2.2]octane-7-carboxylic acid γ-lactone hydrobromide are dissolved in 3 ml. of water, and the pH is adjusted to 8–9 with a saturated aqueous ammonium hydroxide solution. The aqueous solution is extracted with three 5-ml. portions of dichloromethane, and the combined dichloromethane phases are dried over magnesium sulfate. The mixture is then evaporated in vacuo, on a water bath of 30° to 40° C. The obtained oil is dissolved in 6 ml. of absolute chloroform, and 0.669 g. (0.00298 moles) tryptophyl bromide are added. The reaction mixture is heated on an oil bath of 100° to 110° C. for one hour. The concentrated reaction mixture is dissolved by the addition of 5 ml. of dichloromethane and 2 ml. of water. The organic phase is extracted with three 2-ml. portions of water. The dichloromethane phase is dried over magnesium sulfate, and evaporated in vacuo.

Yield: 0.34 g. (0.000864 moles), 35%.

t.l.c. (Kieselgel 60 F$_{254}$; 10:1 benzene/acetone; development in UV light of 254 nm or in iodine vapor): R$_f$: 0.7

Melting point: 134° to 147° C.

EXAMPLE 28

N-[2-(3'-Indolyl)-ethyl]-4-ethyl-7-chloro-7-methoxycarbonyl-2-azabicyclo[2.2.2]oct-5-ene 10.3 g. (0.033 moles) of 4-ethyl-7-chloro-7-methoxycarbonyl-2-azabicyclo[2.2.2]oct-5-ene, 7.4 g. (0.033 moles) of tryptophyl bromide and 19 ml. of triethyl amine are dissolved in 80 ml. of absolute methanol. The reaction is carried out at room temperature and monitored by thin layer chromatography (Kieselgel 60 F$_{254}$ plate) until tryptophyl bromide is completely used up, using a 10:1 mixture of benzene and acetone as an eluent, and a new product can be detected with a 8:4:2 mixture is benzene, chloroform and ethanol. The reaction mixture is evaporated in vacuo. To the residual oil 100 ml. of water are added, and the obtained mixture is extracted with three 100-ml. portions of benzene. The combined benzene phases are dried over magnesium sulfate, filtered and evaporated. If according to t.l.c. the reaction mixture does not contain any decomposition product, the desired product is crystallized from a 96% ethanol. If the reaction mixture is contaminated with by-products due to decomposition, the crude product is purified by column chromatography.

Yield: 3.8 g. (1.0 mmole) 31% t.l.c. (Kieselgel 60 F$_{254}$; eluent: 10:1 mixture of benzene and acetone and 8:4:2 mixture of benzene, chloroform and ethanol, resp.; development: in UV light of 254 nm or in iodine vapor): R$_f$: 0.75.

IR spectrum, cm$^{-1}$: 3300 indole NH, 1720 ester C=O.

NMR spectrum (CDCl$_3$) ppm: 6.2–6.8 (m H$_1^5$+H$_1^6$), 7.05–7.7 (m Ar+indole H$_1^2$), 3.8 (d H$_1^1$).

EXAMPLE 29

N-[2-(3'-Indolyl)-ethyl]-4-ethyl-5-bromo-6-hydroxy-7-chloro-2-azabicyclo[2.2.2]octane-7-carboxylic acid γ-lactone 0.26 g. (0.0009849 moles) of 4-ethyl-5-bromo-6-hydroxy-7-chloro-2-azabicyclo[2.2.2]octane-7-carboxylic acid γ-lactone hydrobromide are dissolved in 2 ml. of methanol. To the solution 0.15 ml. (0.143 moles) of triethyl amine and 0.22 g. (0.00098 moles) tryptophyl bromide are added. The reaction mixture is stirred on an oil bath of 60° C., under protection from light, for one day. The progress of the reaction is monitored by thin layer chromatography (Kieselgel 60 plate, 10:1 benzene/acetone; development in iodine vapor). When the reaction is complete, the R$_f$=0.76 peak corresponding to tryptophyl bromide disappears and a new peak appears at R$_f$=0.5, corresponding to the desired product. The reaction mixture is evaporated in vacuo, on a water bath of 40° to 45° C. The evaporation residue is column chromatographed on a 30-fold amount of Kieselgel 60 (0.063–0.2 mm.), using a 10:1 mixture of benzene and acetone as an eluent.

Yield: 0.15 g. (0.0003435 moles), 34.8% t.l.c. (Kieselgel 60 F$_{254}$; 10:1 benzene/acetone; development in iodine vapor): R$_f$=0.5

IR (film) cm$^{-1}$: 3300 indole NH; 1820 C=O;
(KBr) 3450 indole NH; 1820 C=O

NMR spectrum (CDCl$_3$) ppm: 7.05–7.7 (m, Ar H+indole H$_1^2$), 4.4 (d H$_1^5$); 3.45 (triplet H$_1^1$); 3.3 (m, H$_2^3$); 2.4 (m H$_2^8$).

NMR spectrum (CDCl$_3$, base) ppm: 4.4 (d, H$_1^5$); 3.45 (triplet H$_1^1$); 3.3 (m H$_2^3$); 2.4 (m H$_2^8$).

EXAMPLE 30

N-[(3'-Indolyl)-acetyl]-7-chloro-7-methoxycarbonyl-2-azabicyclo[2.2.2]oct-5-ene 5.8 g. (0.03 moles) of indolyl-3-acetic acid and 4.6 ml. (3.3 g., 0.033 moles) of triethyl amine are dissolved in 97 ml. of dimethyl formamide. The solution is cooled to −5° C. to −10° C., and 4.1 ml. (4.1 g., 0.034 moles) of pivalyl chloride are added dropwise, at the above temperature. After stirring for 20 minutes a thick suspension is obtained. To the suspension a solution of 8.0 g. (0.0284 moles) of 7-chloro-7-methoxycarbonyl-2-azabicyclo[2.2.2]oct-5-ene hydrobromide and 4.6 ml. (3.3 g., 0.033 moles) of triethyl amine in 97 ml. of dimethyl formamide is added at a temperature between 0° C. and −5° C. The reaction mixture is then allowed to warm up to room temperature, and stirred for an additional hour. The precipitated triethyl amine hydrochloride and hydrobromide, resp. is filtered off and washed with 5 ml. of dimethyl formamide. The mother liquor is evaporated in vacuo. The evaporation residue is dissolved in 400 ml. of ethyl acetate, washed with two 40-ml. portions of water, and dried over sodium sulfate. The ethylacetate solution is evaporated, and the precipitated crystalline product is filtered off. Yield: 8.5 g. The crude product is dissolved in a mixture of 250 ml. of chloroform and 60 ml. of methanol and the solution is evaporated. The precipitated crystalline product is filtered off and washed with 10 ml. of chloroform.

Yield: 8.1 g. (0.0226 moles), 68%.

Melting point: 201°–202° C.

IR spectrum (KBr) cm$^{-1}$: ester C=O 1720, acid amine C=O 1640

NMR spectrum: 7.0–7.7 ppm; indole aromatic; 5.8 and 6.4 ppm: m ($H_5^1 + H_6^1$) 3.75 ppm (s—OCH$_3$).

Mass spectrum m/z: M=358, 322, 301, 299, 238, 157, 130, 121, 119, 117, 103, 93, 91, 81, 80, 77

EXAMPLE 31

N-[(3'-Indolyl)-acetyl]-7-chloro-7-cyano-2-azabicyclo[2.2.2]oct-5-ene

Following the procedure described in Example 30 but starting from 8.0 g. (0.032 moles) of 7-chloro-cyano-2-azabicyclo[2.2.2]oct-5-ene hydrogen bromide, the title compound is obtained.

Yield: 4.65 g. (0.0143 moles) 44.6%

Melting point: 176° C.

IR spectrum (IBr): acid amide C=O 1640 cm$^{-1}$, cyano 2230 cm$^{-1}$

NMR spectrum: 7.0–7.7 ppm, indole aromatic, 6.6 m ($H_5^1 + H_6^1$)

Mass spectrum m/z: M=325, 389, 238, 158, 157, 130, 121, 117, 116, 103, 102, 93, 81, 80, 77.

t.l.c. (Kieselgel 60 F$_{254}$ plate, eluent: 10:1 mixture of chloroform and methanol, development in UV light of 254 nm or iodine vapor): R$_f$=0.7

EXAMPLE 32

N-[(3'-Indolyl)-acetyl]-6-chloro-6-methoxycarbonyl-2-azabicyclo[2.2.2]octane 7.1 g. of 3-indolyl-acetic acid, 4.2 g. (0.04 moles), 5.75 ml. of triethyl amine are dissolved in 120 ml. of absolute dimethyl formamide. The solution is cooled to a temperature between −5° C. and −10° C., and 4.8 g. (0.04 moles) 4.9 ml.) of pivalyl chloride are added dropwise, at the same temperature. After stirring for 20 minutes a thick suspension is obtained, to which a solution of 11.4 g. (0.04 moles) of 6-chloro-6-methoxycarbonyl-2-azabicyclo[2.2.2]octane hydrobromide and 4.2 g. (0.04 moles) of triethyl amine in 120 ml. of dimethyl formamide is added, between 0° C. and −5° C. When the addition is complete, the mixture is stirred at room temperature for an additional hour. The precipitated solid, which is triethyl amine hydrochloride or hydrobromide, is filtered off and washed with a small amount of dimethyl formamide. The mother liquor is evaporated in a vacuo of 10–20 torr, on a bath of 60° C. To the evaporation residue 400 ml. of ethyl acetate are added, and the mixture is washed with two 40-ml. portions of water, 60 ml. of a 5% sodium bicarbonate solution and finally 60 ml. of a 20% sodium chloride solution, dried over magnesium sulfate, and evaporated. The evaporation residue is recrystallized from 300 ml. of ethanol.

Yield: 9.3 g. (0.026 moles), 65%

Melting point: 195°–196° C.

EXAMPLE 33

N-[(3'-Indolyl)-acetyl]-7-bromo-7-methoxycarbonyl-2-azabicyclo[2.2.2]oct-5-ene 2.2 g. (0.0126 moles) of 3-indolyl-acetic acid are dissolved in 30 ml. of absolute dimethyl formamide. 1.2 g. of triethyl amine are added to the solution, which is then cooled to −5° C. to −10° C. At this temperature 1.6 L g. (0.0126 moles) of pivalyl chloride are added dropwide, under vigorous stirring. The triethyl amine hydrochloride immediately precipitates from the solution. After stirring for 20 minutes a solution of 4.0 g. (0.0126 moles) of 7-bromo-7-methoxycarbonyl-2-azabicyclo[2.2.2]oct-5-ene hydrobromide and 1.2 g. of triethyl amine in 20 ml. of dimethyl formamide is added. The mixture is stirred at room temperature for an additional hour, and the hydrochloride or hydrobromide of the precipitated triethyl amine is filtered off. The mother liquor is evaporated in vacuo, on an oil bath of 60° C. The evaporation residue is dissolved in 300 ml. of dichloromethane and washed with 100 ml. of water. The dichloromethane phase is dried over magnesium sulfate, and evaporated in vacuo. The evaporation residue is crystallized from acetone.

Yield: 2.0 g. (0.005 moles) 40% t.l.c. (Kieselgel 60 F$_{254}$, eluent: a 8:4:2 mixture of benzene, chloroform and ethanol, development: in UV light of 254 nm or in iodine vapor) R$_f$=0.85

IR spectrum (KBr) cm$^{-1}$: 3250 NH, 1720 ester C=O, 1620 N—C=O

NMR spectrum (CDCl$_3$+DMSO d$_6$) ppm: 7.7–7.3 indole aromatic, 6.6 m ($H_1^5 + H_1^6$), 5.0 (m $H_1^1$).

The new compounds of the formula (I) possess immunosuppressive, anticonvulsive, vasodilating and gastric acid secretion inhibiting properties. Preferably the new compounds are orally administered to a patient in need of such treatment. The compounds are preferably administered in the form of a pharmaceutical composition which contains besides a pharmaceutically effective amount of a compound of the formula (I), a pharmaceutically acceptable inert carrier, diluent, or excipient.

The new compounds of the formula (I) are orally administered to a patient, preferably in a dosage of 25 to 100 mg day.

One of the best compounds of the formula (I) for exerting an immunosuppressive effect is N-[2-(3'-indolyl-ethyl)]-7-chloro-7-methoxycarbonyl-2-azabicyclo[2,2,2]oct-5-ene of Example 24. It has been found that the LD$_{50}$ value of the compound in mice is 830 mg/kg i.p. and that the ED$_{50}$ value of this compound in mice to exert an immunosuppressive effect is only 8 mg/kg i.p. The ED$_{50}$ value relates to the immunosuppressive effect which was measured according to the method of G. Takatsy and J. Fueresz, Acta. Microbiol. Acad. Sci. Hung., 3, 105, (1955) or J. Cottney et al, Agents and Actions, 10, 43 (1980).

The new compounds of the formula (I) can also be converted into known cytostatic compounds by methods wellknown to those "skilled in the art." The cytostatic compounds belong to the iboga alkaloid series. For instance, N-[(3'-indolyl)-acetyl]-7-chloro-7-methoxycarbonyl-2-azabicyclo[2,2,2]oct-5-ene of Example 30 can be converted according to Szantay et al, Tetrahedron Letters, 24, 5539, (1983) to (+ −)-oxo-20-deethyl-catharantine which can be further converted according to the method of R. J. Sundberg and J. D. Bloom, J. Org. Chem. 45, 3382 (1980) to (+ −)-20-deethyl-catharantine.

The latter can be condensed with vindoline according to the method of F. Gueritte et al, J. Org. Chem 46, 5393 (1981) to form 20-deethyl-anhydro-vinblastine possessing cytostatic activity.

The compunds of the formula (I) having the formula (Ia)

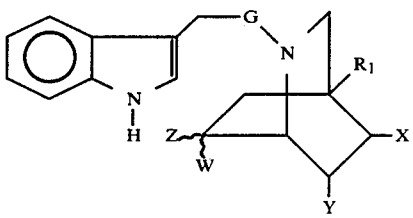

(Ia)

in which

G is >CH₂ or >C=O;

Z is halo;

W is alkoxycarbonyl having 1 to 4 carbon atoms in the alkoxy group, or cyano;

R₁ is hydrogen or C₁–C₄ alkyl; and

X and Y each stand for hydrogen, or together form a C—C bond, can also be converted into new indolo[2,3-b]quinolizines of the formula (IV)

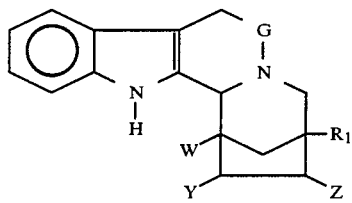

(IV)

and new indolo[2,3-g]cyclopent[a]indolizines of the formula

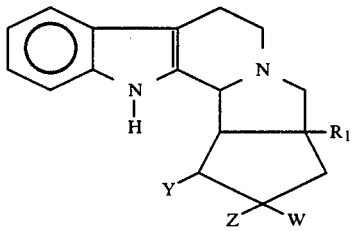

(V)

The new compounds of the formula (IV) and (V) have the ability to inhibit gastric acid secretion and are used in the treatment of ulcers caused by gastric acid. Preferably the compounds are administered to the patient orally. In fact the compounds of the formula (IV) and/or (V), pharmaceutical compositions containing same, and a process for the preparation of the new compounds are the subject of applicants' copending Hungarian patent application 2342/83 filed 29 June 1983 as well as the subject of their copending U.S. application having Ser. No. 625,071.

To prepare compounds of the formula (IV) where G is a >CH₂ group as well as compounds of the formula (V), compounds of the formula (Ia) where G is a >CH₂ group are heated in an organic solvent to obtain a mixture of the formula (IV) and (V) compounds which may be separated.

To prepare compounds of the formula (IV) where G is a >C=O group, the corresponding compound of the formula (Ia) is reacted with a complexing agent, in an organic solvent, under anhydrous conditions. Preferably the complexing agent is silver tetrafluoroborate or silver hexafluoroantimonate and the organic solvent is apolar.

The following Examples 34–47 are directed to the preparation of compounds of the formulae (IV) and/or (V) from the compounds of the formula (Ia).

EXAMPLE 34

Methyl 1,3-vinylene-1,3,4,6,7,12b-hexahydro-2H,12H-indolo[2,3-a]quinolizinyl-1-carboxylate 1 g. ($3.24 \times 10^{-3}$ moles) of N-[(3-indolyl)-ethyl]-7-chloro-7-methoxycarbonyl-2-azabicyclo[2.2.2]oct-5-ene is dissolved in 10 ml. of tert.-butanol and the solution is stirred at boiling temperature (83° C.) for 24 hours. It is then evaporated in vacuo and chromatographed on a Kieselgel 60 column, using a 8:4:2 mixture of toluene, chloroform and ethanol as eluent. The obtained mixture of the compounds of the formulae (II) and (III) is subjected to column chromatography on an Al₂O₃ column, using a 1:1 mixture of ethyl acetate and chloroform as eluent. 0.25 g. ($9.2 \times 10^{-4}$ moles) of the title compound are obtained as oil which solidifies.

Yield: 28.4%

IR(KBr): 3340 (indole NH), 1720 (C=O) cm⁻¹

¹H NMR (CDCl₃): 7.55–7.0 (m, 4H, aromatic H-s); 6.32–6.05 (d, 2H, olefin H-s); 3.95 (br, 3H, OCH₃) ppm.

¹³C NMR (CDCl₃): $C_1$ (57.59s), $C_2$ (40.24t), $C_3$ (40.24d), $C_4$ (45.41t), $C_6$ (50.29t), $C_7$ (17.54t), $C_{7a}$ (110.74s), $C_{7b}$ (127.2s), $C_8$ (118.02d), $C_9$ (121.83d), $C_{10}$ (119.37d), $C_{11}$ (111.24d), $C_{11}$ (131.76s), C $C_{12a}$ (136.01s), $C_{12b}$ (55.09d), $C_{13}$ (134.94d), $C_{14}$ (132.8d) ppm.

MS m/e/80° C.: 308(10,M), 243 (4.4), 241 (5.0), 220 (46.0), 200 (3.0), 184 (35.0), 256 (17.0) %.

EXAMPLE 35

Methyl 3a,4,6,7,12b,12c-hexahydro-3H,12H-indolo[2,3-g]cyclopent[a]indolizine-2-carboxylate 1 g. ($3.24 \times 10^{-3}$ moles) N-[(3-indolyl)-ethyl]-7-chloro-7-methoxycarbonyl-2-azabicyclo[2.2.2]oct-5-ene is dissolved in 10 ml. of n-butanol and the solution is stirred at 110° C. for 5 hours. The progress of the reaction is monitored by thin layer chromatography. The reaction mixture is evaporated in vacuo, and chromatographed on a Kieselgel 60 column, using a 8:4:2 mixture of toluene, chloroform and ethanol as eluent. Yield: 0.47 g. (53%)

IR(KBr): 3320 (indole NH), 1720 (C=O) cm⁻¹

¹H NMR (CDCl₃): 7.55–7.0 (m, 4H, aromatic H-s); 6.25 (d, 1H, olefin); 3.95 (s, 3H, OCH₃) ppm ¹³C NMR (CDCl₃): $C_1$ (149.8d), $C_2$ (112.7s), $C_3$ (39.6t), $C_{3a}$ (41.4d), $C_4$ (45.8t), $C_6$ (50.29t), $C_7$ (17.54t), $C_{7a}$ (110.7s), $C_{7b}$ (127.2s), $C_8$ (118.02d), $C_9$ (121.83d), $C_{10}$ (119.37d), $C_{11}$ (111.2d), $C_{11a}$ (131.76s), $C_{12a}$ (136.02s), $C_{12b}$ (62.6d), $C_{12c}$ (56.8d) ppm.

MS m/e: 308 (10 m), 243 (1.4), 241 (1.5), 220 (2.8), 200 (4.8), 184 (100), 169 (3.9) %.

EXAMPLE 36

Methyl 3a,4,6,7,12b,12c-hexahydro-3H,12H-indolo[2,3-]cyclopent[a]indolizine-2-carboxylate.

0.25 g of methyl 1,3-vinylene-1,3,4,6,7,12b-hexahydro-2H,12H-indolo[2,3-a]quinolizinyl-1-carboxylate prepared in Example 34 are dissolved in 12 ml of toluene and boiled (111° C.) for 3 hours. The end-product is isolated from the reaction mixture as described in Example 35. The physical characteristics of the product obtained are identical with those given in Example 35.
Yield: 0.19 g (76%).

EXAMPLE 37

2-Cyano-3a,4,6,7,12b,12c-hexahydro-3H,12H-indolo[2,3-g]cyclopent[a]indolizine.

1 g ($3.2 \times 10^{-3}$ moles) of N-[(3-indolyl)-ethyl]-7-chloro-7cyano-2-azabicyclo[2,2,2]oct-5-ene is dissolved in 1.5 ml of diethylene glycole at 80° C., and the solution is stirred at 160° C. for 20 minutes. The progress of the reaction is monitored by thin layer chromatography. The reaction mixture is cooled to 20° C., diluted with 15 ml of acetone and the product obtained is isolated in a crystalline form (melting point: 234° to 237° C.).

Yield: 0.2 g (22%)
IR (KBr): 3320 (indole NH), 2230 (CN) cm$^{-1}$
$^1$H NMR (CDCl$_3$+DMSO): 7.77–7.1 (m, 4H, aromatic H-s); 6.85 (d, 1H, olefin); 4.1 (d, 1H, N-CH); 3.65 (m, 1H, CH beside olefin) ppm.
$^{13}$C NMR (CDCl$_3$+DMSO): C$_1$ (149.8d), C$_2$ (114.8s), C$_3$ (39.6t), C$_{3a}$ (41.4d), C$_4$ (45.8t), C$_6$ (57.1d), C$_7$ (17.6t), C$_{7a}$ (106.77s), C$_{7b}$ (126.97s), C$_8$ (117.91d), C$_9$ (121.07d), C$_{10}$ (118.72d), C$_{11}$ (110.99d), C$_{11a}$ (133.54s), C$_{12a}$ (136.37s), C$_{12b}$ (62.6d), C$_{12c}$ (56.8d) ppm.
MS m/e: 276 (10.1), 275 (23 M), 274 (6), 185 (23), 184 (100), 183 (11), 169 (7) %.

EXAMPLE 38

Methyl 3-ethyl-3a,4,6,7,12b,12c-hexahydro-3H,12H-indolo[2,3-]cyclopent[a]indolizine-2-carboxylate 1 g. of N-[3-indolyl)-ethyl]-7-chloro-7-methoxycarbonyl-4-ethyl-2-azabicyclo[2.2.2]oct-5-ene is dissolved in 20 ml. of methanol, and the solution is refluxed in nitrogen atmosphere. The progress of the reaction is monitored by thin layer chromatography. When the total amount of the starting material is used up, the reaction mixture is evaporated in vacuo, and the oily product is chromatographed on a Kieselgel 60 chromatographic column, using a 8:4:2 mixture of benzene, chloroform and ethanol as eluent. The product is crystallized from a 96% ethanolic solution of sulfuric acid in the form of its sulfate salt.

Melting point: 285° to 288° C.
Yield: 0.3 g. (37%)
IR (KBr): 3340 (indole NH), 1720 (C=O) cm$^{-1}$
$^1$H NMR (CDCl$_3$): 7.65–7.0 (m, 4H, aromatic H-s); 6.95 (d, 1H, olefin); 3.8 (d, 1H, CH-N); 0.9 (t, 3H, CH$_2$-CH$_3$) ppm
MS m/e: 336 (M 13), 335 (2.3), 321 (2.9), 305 (46), 184 (100), 169 (5.2) %

EXAMPLE 39

2-Cyano-3-ethyl-3a,4,6,7,12b,12c-hexahydro-3H,12H-indolo[2,3-g]cyclopent[a]indolizine 1 g. ($2.85 \times 10^{-3}$ moles) of N-[(3-indolyl)ethyl]-7-chloro-7-cyano-4-ethyl-2-azabicyclo[2.2.2]oct-5-ene is dissolved in 20 ml. of n-butanol and the solution is refluxed for 6 hours. The progress of the reaction is monitored by thin layer chromatography. When the total amount of the starting substance is used up, the mixture is evaporated in vacuo, and the obtained oily product is subjected to column chromatography as described in Example 38.

Yield: 0.2 g. (23%)

IR (KBr): 3340 (indole NH), 2230 (CN) cm$^{-1}$
$^1$H NMR (CDCl$_3$): 7.78–7.13 (m, 4H, olefin H-s); 6.9 (d, 1H, olefin); 3.75 (d, 1H, CH-N); 0.9 (t, 3H, CH$_2$-CH$_3$) ppm.
MS m/e: 303 (12M), 302 (2.5), 288 (2.7), 272 (48), 184 (100) %

EXAMPLE 40

Methyl 1,3-ethylene-1,3,4,6,7,12b-hexahydro-2H,12H-indol[2,3-a]quinolizinyl-1-carboxylate 0.1 g. ($2.88 \times 10^{-4}$ moles) of N-[(3-indolyl)ethyl]-6-chloro-6-methoxycarbonyl-2-azabicyclo[2.2.2]-octane are dissolved in 1 ml. of diethylene glycole at 190° C., and the solution is stirred for 20 minutes. The product obtained is separated by column chromatography as described in Example 38 (eluent: a 8:4:2 mixture of toluene, chloroform and ethanol), isolating the product obtained at R$_f$=0.62.

Melting point: 148° to 151° C.
Yield: 0.03 g. (33.5%)
IR (KBr): 3320 (indole NH), 1720 (C=O) cm$^{-1}$
$^1$H NMR (CDCl$_3$): 7.55–7.0 (m, 4H, aromatic H-s); 3.85 (s, 3H, OCH$_3$) ppm.
$^{13}$C NMR (CDCl$_3$): C$_1$ (52.83s, 34.57t), C$_3$ (36.12d), C$_4$ (51.94t), C$_6$ (50.61t), 17.01t), C$_{7a}$ (109.65s), C$_{7b}$ (127.39s), C$_8$ (118.02d), C$_9$ (121.66d), C$_{10}$ (119.37d), C$_{11}$ (111.24d), C$_{11a}$ (132.7a), C$_{12a}$ (135.95s), C$_{12b}$ (t1.55d), C$_{13}$ (28.65t), C$_{14}$ (36.56t) ppm
MS m/e: 310 (58. M), 309 (100), 295 (2), 279 (3.8), 259 (0.5), 251 (2), 239 (1.5), 223 (1.9), 211 (15), 185 (7), 187 (7), 182 (10) %

EXAMPLE 41

Methyl 1,3-vinylene-1,3,4,6,7,12b-hexahydro-2H,12H-indolo[2,3-a]quinolizine-6-one-1-carboxylate 1 g. ($2.5 \times 10^{-3}$ moles) of N-[(3-indolyl)-acetyl]-7-bromo-7-methoxycarbonyl-2-azabicyclo[2,2,2]oct-5-ene is dissolved in 40 ml. of dry dichloromethane. To this solution a solution of silver tetrafluoroborate in benzene is added under continuous stirring, and the mixture is stirred at room temperature. The progress of the reaction is monitored by thin layer chromatography. The inorganic compounds are eliminated from the reaction mixture with 5 ml. of a saturated sodium bicarbonate solution, the organic phase is dried, evaporated in vacuo, and the components are separated by column chromatography as described in Example 38 and isolated as a colorless oil.

IR (film): 3400 (indol NH), 1720 (C+O), 1600 (N—C=O) cm$^{-1}$
$^1$H NMR (CDCl$_3$): 7.55–7.07m, 4H, aromatic H-s); 6.32–5.81 (d, m, 2H, olefin); 5.23–4.71 (t and 2xm, 2H, N—CH$_2$—); 3.81 (s, 3H, OCH$_3$) ppm
$^{13}$C NMR (CDCl$_3$): C$_1$ (60.56s, 43.19t), C$_3$ (39.54d), C$_4$ (49.90t), C$_6$ (169.92s), C$_7$ (29.25t), C$_{7a}$ (106.79s), C$_{7b}$ (126.69s), C$_8$ (118.45d), C$_9$ (122.88d), C$_{10}$ (119.83d), C$_{11}$ (116.16d), C$_{11a}$ (125.29s), C$_{12a}$ (136.59s), C$_{12b}$ (59.25d), C$_{13}$ (136.97d), C$_{14}$ (130.05d) ppm.
MS m/e: 322 (45.M), 305 (6), 291 (4), 198 (80), 185 (10), 184 (52), 170 (100), 169 (86), 115 (11) %.

EXAMPLE 42

Methyl 1,3-ethylene-1,3,4,6,7,12b-hexahydro-2H,12H-indolo[2,3-a]quinolizine-6-one-1-carboxylate 0.45 g. (1.26×10$^{-3}$ moles) of N-[(3-indolyl)acetyl]-6-chloro-6-methoxycarbonyl-2-azabicyclo[2,2,2]octane are reacted with silver tetrafluoroborate. Furtheron the procedure described in Example 41 is followed. The end-product is isolated as a colorless oil.

IR (film): 3400 (NH), 1700 (C=O), 1600 (N—C=O)

$^1$H NMR (CDCl$_3$): C$_1$ (57.89s), C$_2$ (31.88t), C$_3$ (36.09d), C$_4$ (50.23t), C$_6$ (168.57s), C$_7$ (29.19t), C$_{7a}$ (107.00s), C$_{7b}$ (126.31s), C$_8$ (118.43d), C$_9$ (122.87d), C$_{10}$ (119.94d), C$_{11}$ (110.90d), C$_{11a}$ (125.29s), C$_{12a}$ (136.85s), C$_{12b}$ (63.77d), C$_{13}$ (31.15t), C$_{14}$ (32.92t) ppm MS m/e: 324 (100, M), 307 (24), 293 (5.3), 292 (4.3), (6.5), 225 (9.4) 199 (11), 198 (15), 184 (8.2), 171 (47) %.

EXAMPLE 43

2-Cyano-1,2,3a,4,6,7,12b,12c-octahydro-3H,12H-indolo[2,3-g]cyclopent[a]indolizine 0.27 g. (1×10$^{-3}$ moles) of 2-cyano-3a,4,6,7,12b-hexahydro-3H,12H-indolo[2,3-g]cyclopent[a]indolizine are dissolved in 5 ml. of methyl alcohol, and this solution is added to a prehydrogenated solution of 0.05 g. of a 10% palladium-on-charcoal catalyst in 2 ml. of methanol, and hydrogen gas is bubbled through the reaction mixture under vigorous stirring. The progress of the reaction is followed by thin layer chromatography, the catalyst is filtered off, washed with methanol and the combined alcoholic phases are evaporated in vacuo to yield 0.25 g. of an oily product.

IR (KBr): 3320 (indole NH), 2230 (CN) cm$^{-1}$.

$^1$H NMR (CDCl$_3$): 7.65–7.05 (m, 4H, aromatic H-s) 4.1 (d, 1H, N—CH) ppm $^{13}$C NMR (CDCl$_3$): C$_1$ (40.07t), C$_2$ (42.78d), C$_3$ (39.65t), C$_{3a}$ (41.37d), C$_4$ (45.85t), C$_6$ (50.29t), C$_7$ (17.57t), C$_{7a}$ (110.7s), C$_{7b}$ (127.2s), C$_8$ (118.02d), C$_9$ (121.83d), C$_{10}$ (119.37d), C$_{11}$ (111.2d), C$_{11a}$ (137.72s), C$_{12a}$ (136.15s), C$_{12b}$ (62.47d), C$_{12c}$ (56.78d) ppm MS m/e: 277 (58, M), 276 (66), 252 (2.9), 251 (3), 209 (7.5), 184 (100), 169 (11) %

EXAMPLE 44

Methyl 1,2,3a,4,6,7,12b,12c-octahydro-3H,12H-indolo[2,3-g]cyclopent[a]indolizine-2-carboxylate 0.052 g. of methyl 3a,4,6,7,12b,12c-hexahydro-3H,12H-indolo[2,3-g]cyclopent[a]indolizine-2-carboxylate are reduced as described in Example 43. The obtained product is isolated as an oil.

Yield: 0.048 g. (96%)

IR (KBr): 3320 (indole, NH), 1720 (C=O) cm$^{-1}$ $^1$H NMR (CDCl$_3$): 7.55–7.05 (m, 4H, aromatic, H-s); 3.95 (s, 3H, OCH$_3$) ppm $^{13}$C NMR (CDCl$_3$): C$_1$ (39.6t), C$_2$ (43.2d), C$_3$ (39.85t), C$_{3a}$ (41.25d), C$_4$ (45.87t), C$_6$ (50.35d), C$_7$ (17.54t), C$_{7a}$ (110.76s), C$_{7b}$ (127.23s), C$_8$ (118.12d), C$_9$ (121.83d), C$_{10}$ (119.37d), C$_{11}$ (111.2d), C$_{11a}$ (131.76s), C$_{12a}$ (136.02s), C$_{12b}$ (62.45d), C$_{12c}$ (56.68d) ppm

EXAMPLE 45

Methyl 3-ethyl-1,2,3a,4,6,7,12b,12c-octahydro-3H,12H-indolo[2,3-a]cyclopent[a]indolizine-2-carboxylate Essentially the procedure described in Example 43 is followed except that as starting material methyl 3-ethyl-3a,4,6,7,12b,12c-hexahydro-3H,12H-indolo[2,3-g]cyclopent[a]indolizine-2-carboxylate is employed.

IR (film): 3340 (indole NH), 1720 (C=O) cm$^{-1}$ $^1$H NMR (CDCl$_3$): 7.75–7.13 (m, 4H, aromatic H-s); 3.85 (d, 1H, CH—N); 0.9 (t, 3H, CH$_2$—CH$_3$) ppm MS m/e: 338 (90M), 337 (100), 239 (9), 185 (14), 184 (22), 170 (16), 169 (31) %.

EXAMPLE 46

2-Cyano-3-ethyl-1,2,3a,4,6,7,12b,12c-octahydro-3H,12H-indol[2,3-g]cyclopent[a]indolizine Essentially following the procedure described in Example 43 but starting from 2-cyano-3-ethyl-3a,4,6,7,12b,12c-hexahydro-3H,12H-indolo[2,3-g]cyclopent[a]indolizine the title compound is obtained.

IR (film): 3340 (indole NH), 2230 (CN) cm$^{-1}$ $^1$H NMR (CDCl$_3$): 7.75–7.1 (m, 4H, aromatic H-s); 3.70 (d, 1H, CH-N); 0.9 (t, 3H, CH$_2$-CH$_3$) ppm

EXAMPLE 47

Methyl 1,3-ethylene-1,3,4,6,7,12b-hexahydro-2H,12H-indolo[2,3-a]quinolizinyl-1-carboxylate Essentially following the procedure described in Example 43 but starting from methyl 1,3-vinylene-1,3,4,6,7,12b-hexahydro-2H,12H-indolo[2,3-a]quinolizinyl-1-carboxylate the title compound is obtained.

We claim:

1. 2-Azabicyclo[2.2.2]octane derivatives of the formula

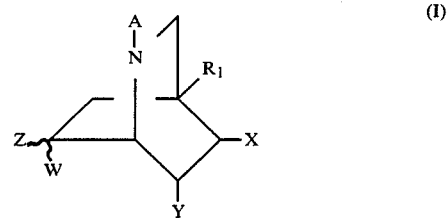

(I)

wherein

A is hydrogen, alkoxycarbonyl having from one to 4 carbon atoms in the alkoxy group, phenylalkoxycarbonyl having from one to 4 carbon atoms in the alkoxy moiety, alkyl having from one to 6 carbon atoms, 3-indolyl-ethyl, 3-indolyl-acetyl or 3-indolyl-acetyl substituted by halogen, lower alkyl or lower alkoxy, R$_1$ is hydrogen or alkyl having from one to 4 carbon atoms, Z is hydrogen or halogen, X is hydrogen or halogen, Y is hydrogen, or X and Y together represent a C—C bond, W is alkoxycarbonyl having from one to 4 carbon atoms in the alkoxy moiety, cyano, carboxamide or haloformyl, or if X stands for halogen, W and Y together represent a

group.

2. An immunosuppressive, which comprises as an active ingredient a pharmaceutically effective amount of at least one compound of the formula (I), as defined in claim 1, in association with a conventional pharmaceutical diluent or excipient.

3. An immunosuppressive method of treatment which comprises the step of administering to an animal subject a pharmaceutically effective amount of the compound of the formula (I) defined in claim 1.

4. The compound of the formula (I) defined in claim 1 which is N-[2-(3'-indolyl-ethyl)]-7-chloro-7-methoxycarbonyl-2-azabicyclo[2,2,2]oct-5-ene.

* * * * *